(12) United States Patent
Potter et al.

(10) Patent No.: US 6,670,524 B1
(45) Date of Patent: Dec. 30, 2003

(54) METHOD FOR PREDICTING FIBER LENGTH USING QTL'S AND MOLECULAR MARKERS

(75) Inventors: Simon Potter, New Westminster (CA); Paul A. Watson, Vancouver (CA)

(73) Assignee: Pulp and Paper Research Institute of Canada, Pointe Claire (CA)

( * ) Notice: Subject to any disclaimer, the term of this patent is extended or adjusted under 35 U.S.C. 154(b) by 0 days.

(21) Appl. No.: 09/494,501

(22) Filed: Jan. 31, 2000

Related U.S. Application Data

(60) Provisional application No. 60/118,103, filed on Feb. 1, 1999.

(51) Int. Cl.$^7$ .............................. A01H 1/00; A01H 1/04; A01H 4/00; C12N 15/10
(52) U.S. Cl. ...................... 800/267; 800/260; 800/263; 800/266; 800/268; 800/269; 800/323; 435/6; 435/91.2
(58) Field of Search ............................ 435/6, 410, 420, 435/422, 91.2; 800/263, 266, 267, 298, 319, 260, 268, 269, 323

(56) References Cited

U.S. PATENT DOCUMENTS

| | | | | |
|---|---|---|---|---|
| 5,523,520 A | * | 6/1996 | Hunsperger et al. | 800/200 |
| 6,054,634 A | * | 4/2000 | O'Malley et al. | 800/267 |

OTHER PUBLICATIONS

Suttan et al. Can. J. For. Res. 24: 278–285, 1994.*
Strauss et al. New Forests 6: 125–158, 1992.*
Bradshaw et al. 1995. Molecular genetics of growth and development in Populus IV. Mapping QTLs with large effects on growth, form, and phenology tratis in a forest tree. Genetics 139:963–973.*
Eshed et al. 1996. Less–than–additive epistatic interactions of quantitative trait loci in tomato. Genetics 143:1807–1817.*
Hemmat et al. 1998. Molecular markers for the scab resistance (Vf) region in apple. J. Amer. Soc. Hort. Soc. 123(6):992–996.*
Kraft et al. 2000. Linkage disequilibrium and fingerprinting in sugar beet. Theor. Appl. Gent. 101:323–326.*
Lansari et al. 1990. A preliminary analysis of self–incompatibility in sour cherry. Hortscience 25(12):1636–1638.*
Michelmore et al. 1991. Identification of markers linked to disease–resistance genes by bulked segregant analysis: a rapid method to detect markers in specific genomic regions by using segregating populations. Proc. Natl. Acad. Sci. (USA) 88:9828–9832.* van Ooijen et al. 1993. An RFLP linkage map of *Lycopersicon peruvianum*. Theor. Appl. Genet. 89:1007–1013.*
Soost et al. 1980. identification of nucellar and zygotic seedlings of citrus with leaf isozymes. Hortscience 15(6):728–729.*
Williams et al. 1992. Conifer wood quality and marker–aided selection: a case study. Can. J. For. Res. 22:1009–1017.*
Xu et al. 1995. A random model approach to interval mapping of quantitative trait loci. Genetics 141;1189–1197.*
J.E. Eckenwalder. "Systematics and Evolution of Populus" in Biology of Populus (Stettler, R.F., Bradshaw, H.D., Heilman, P.E., & Hinckley, T.M. eds) NRC Research Council Press, Ottawa ON, pp. 7–32 (1996).
E.S. Lander & D. Botstein, *Genetics* 121, 185–199 (1989).
L.F. Burkart, *For. Prod. J.*, 16, 52 (1966).
H.D. Bradshaw, M. Villar, B.D. Watson, K.G. Otto & S. Stewart, *Theor. Appl. Genet.* 89, 551–558 (1994).
A.H. Patterson, S. Damon, J.D. Hewitt, D. Zamir & H.D. Rabinowich, *Nature* 335, 721–726 (1988).
H.D. Bradshaw & R.F. Stettler, *Genetics* 139, 963–973 (1995).
G.O. Otegbeye and R.C. Kellison, *Sylvae Genetica* 29, 27 (1980).
C.R.E. Clarke, Msc. Thesis, University of Natal, Pietermaritzburg, South Africa (1990).
R.W. Allard, *Principles of Plant Breeding*. John Wiley & Sons, New York (1960).

* cited by examiner

*Primary Examiner*—David T. Fox
(74) *Attorney, Agent, or Firm*—Ogilvy Renault; France Côté; Christian Cawthorn

(57) ABSTRACT

The present invention relates to a novel method for the prediction of fiber length and the selection of superior trees using genetic marker loci. The method comprises comparing genotypic survey data to phenotypic data collected from the same trees used to create the genotypic survey and identifying particular genetic marker loci or quantitative trait loci (QTL's) that are associated with fiber length. The method allows superior trees to be identified, from both plantations and natural populations, and selected for in tree improvement breeding programs by genotyping with identified genetic marker loci.

6 Claims, 13 Drawing Sheets

FIG_1

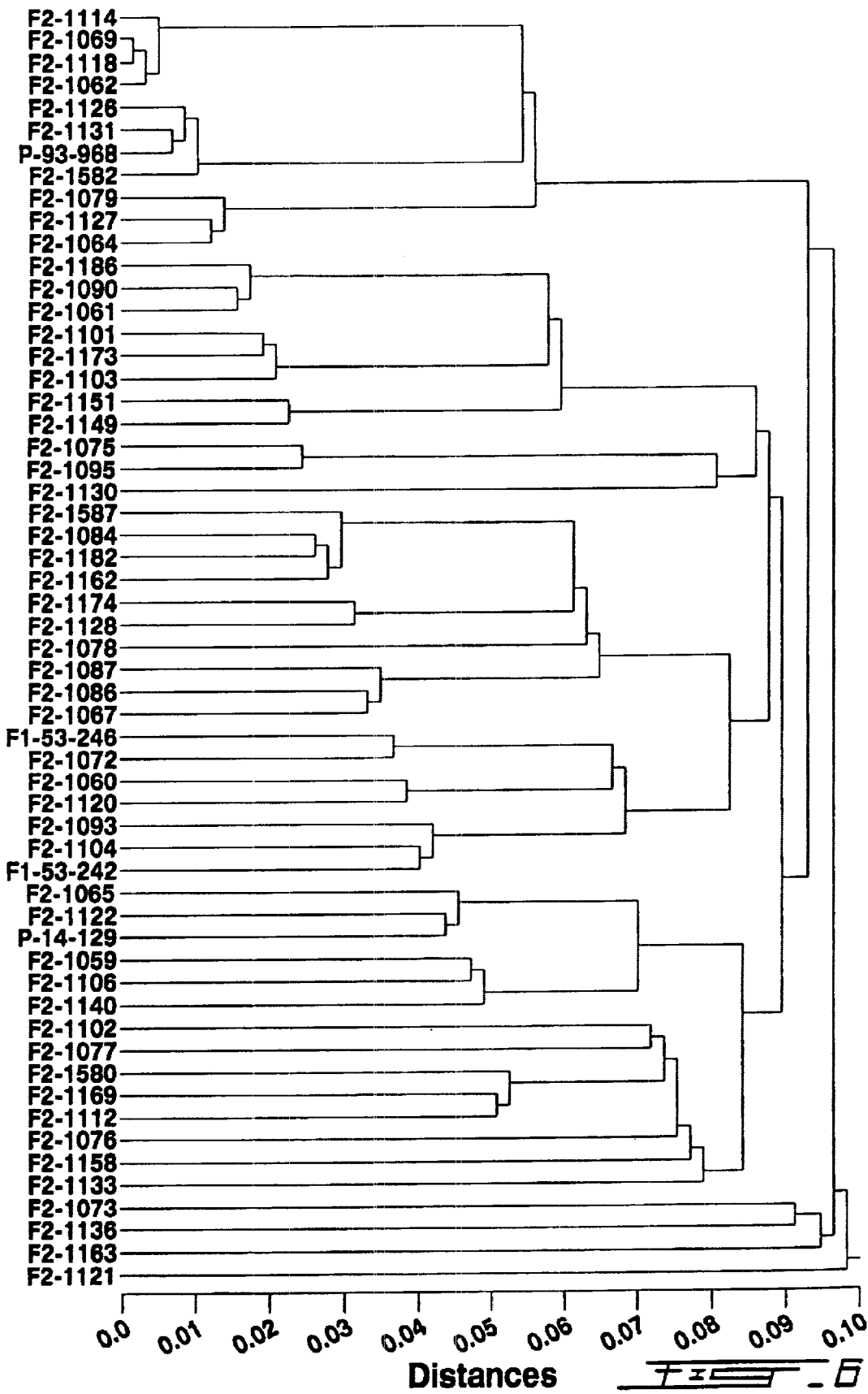

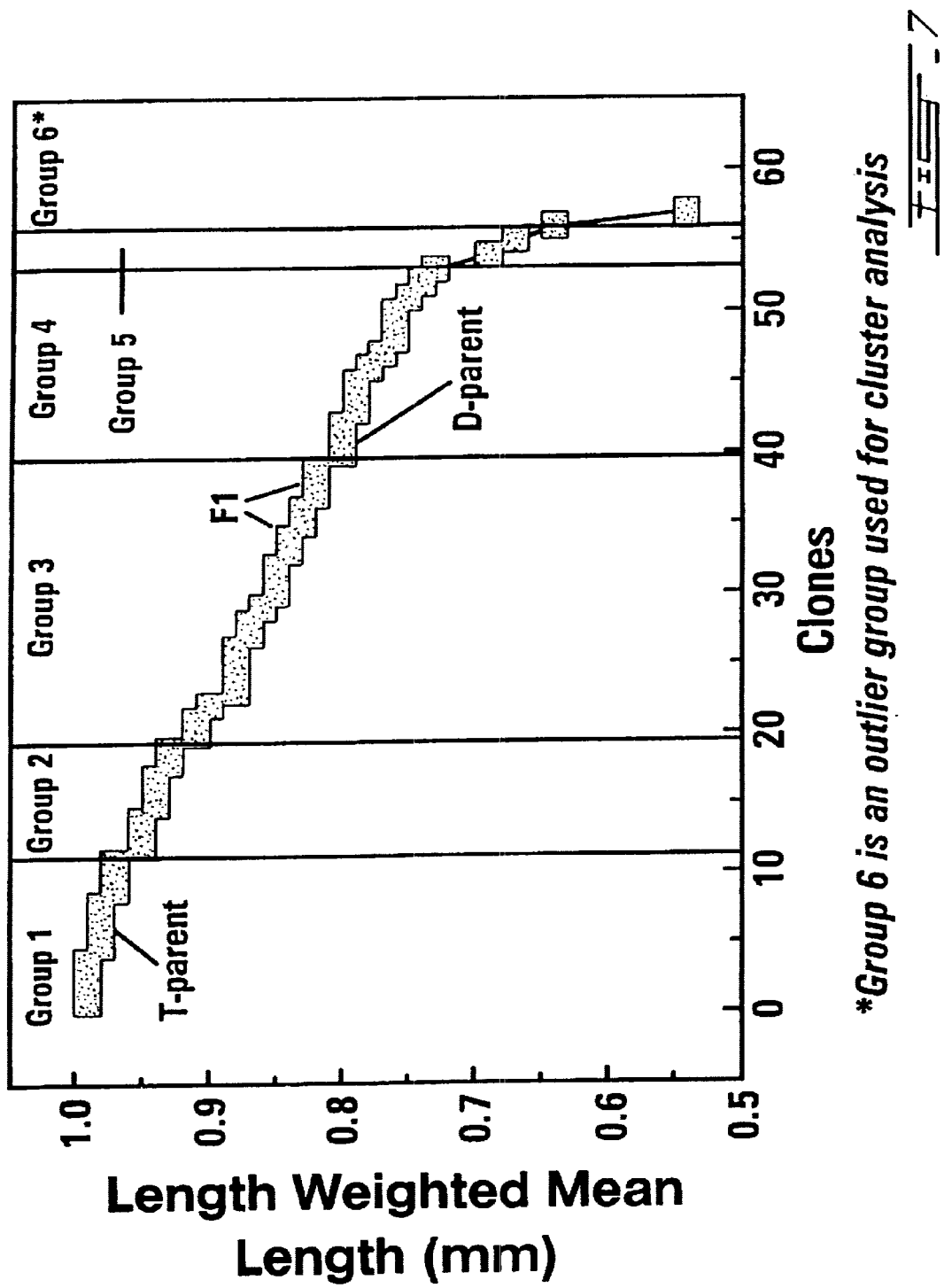

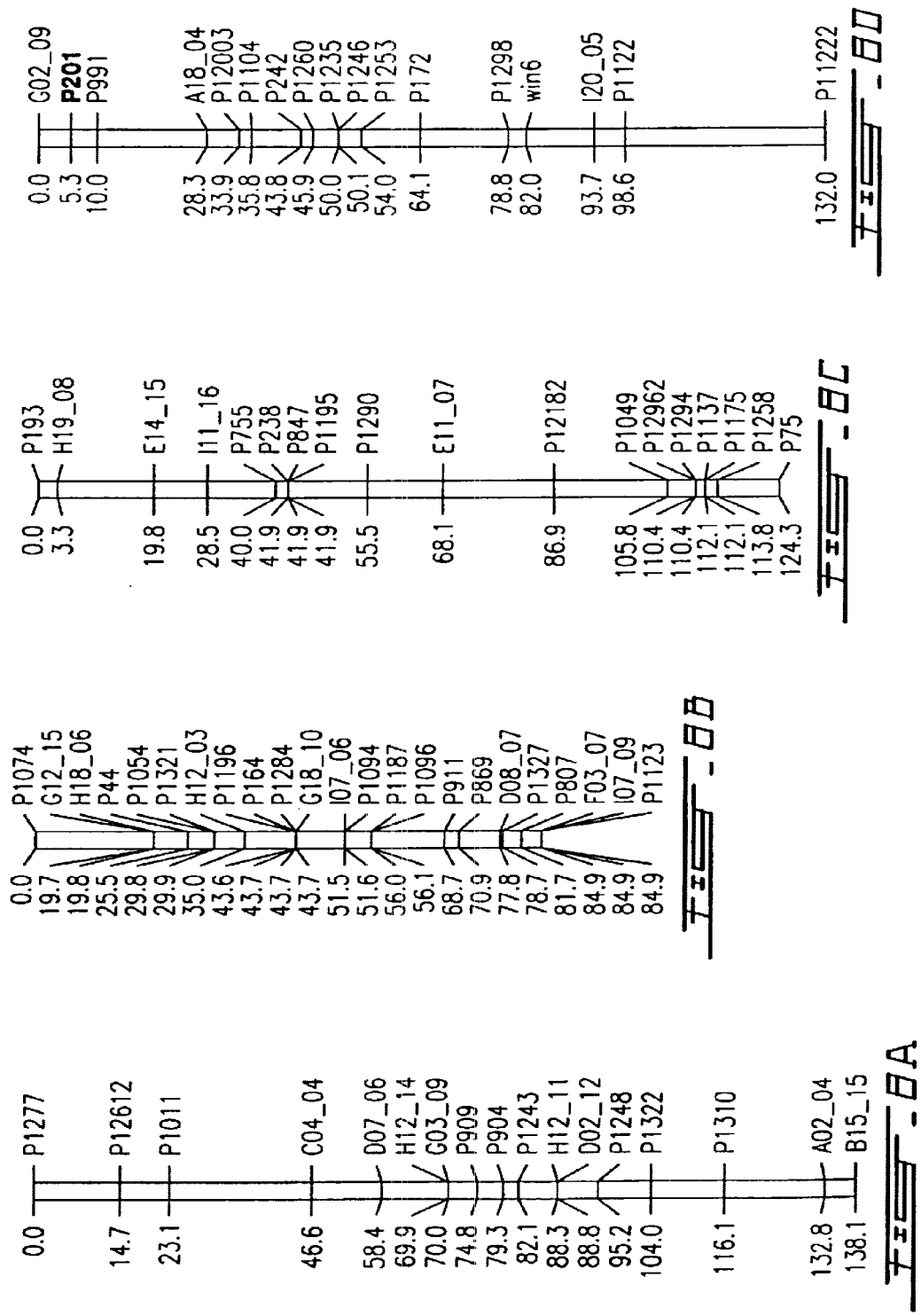

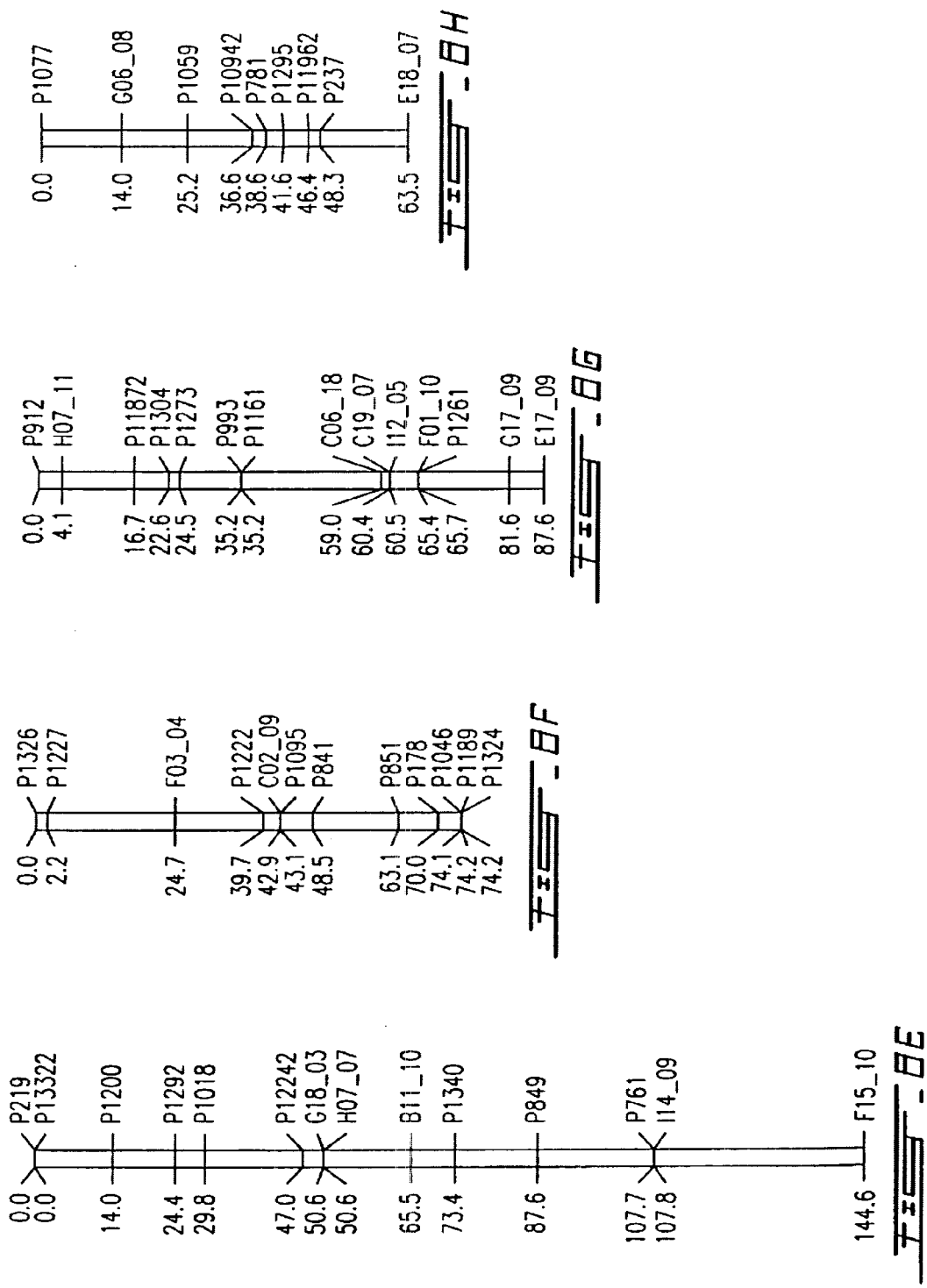

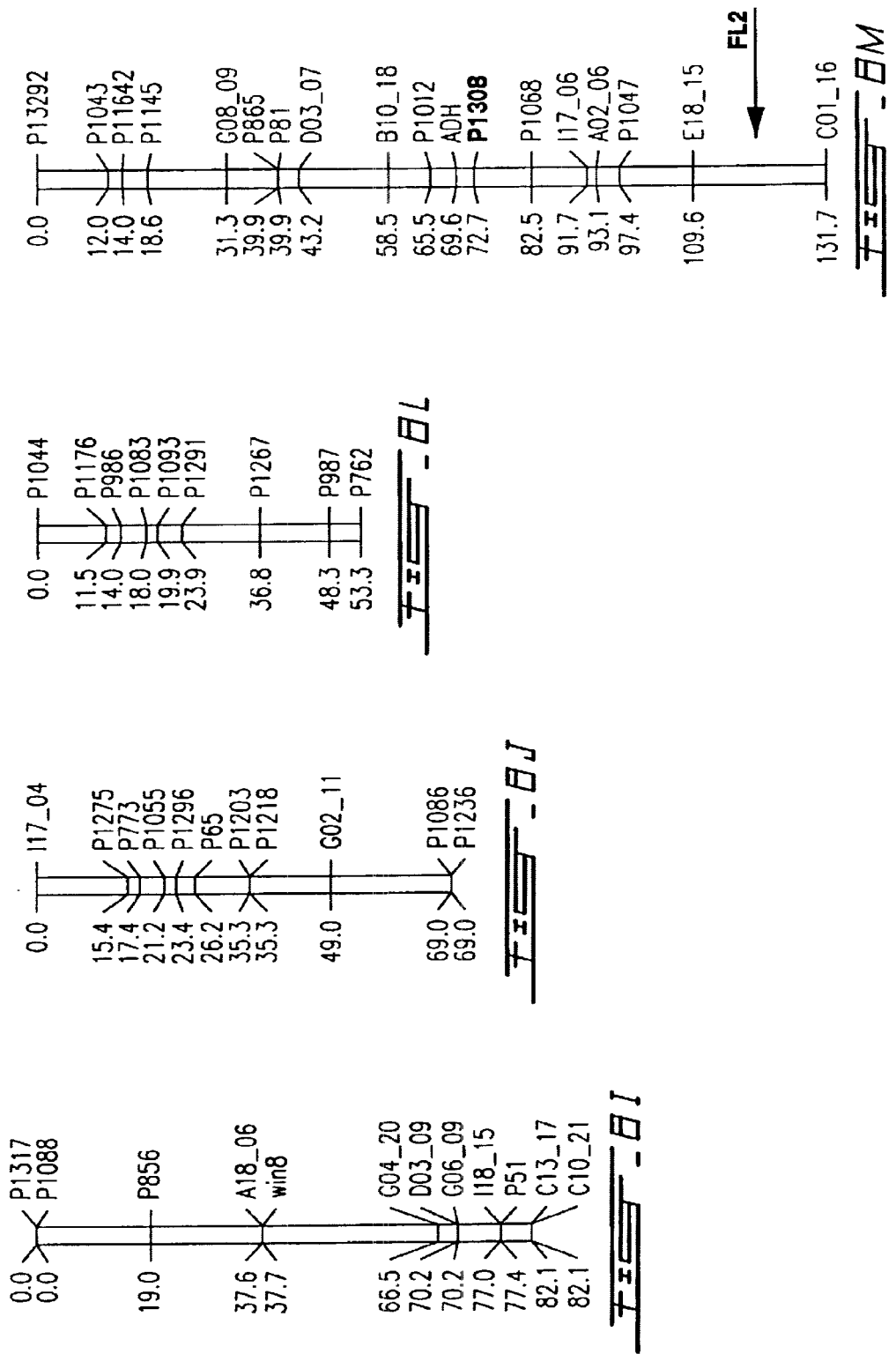

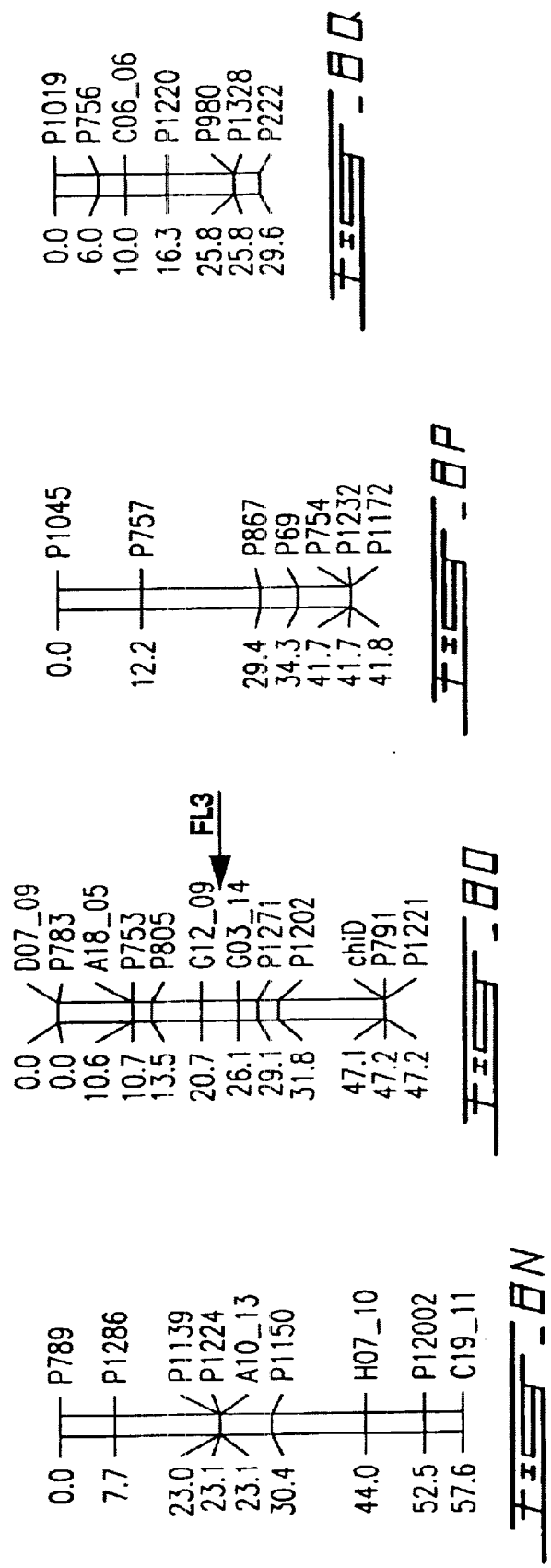

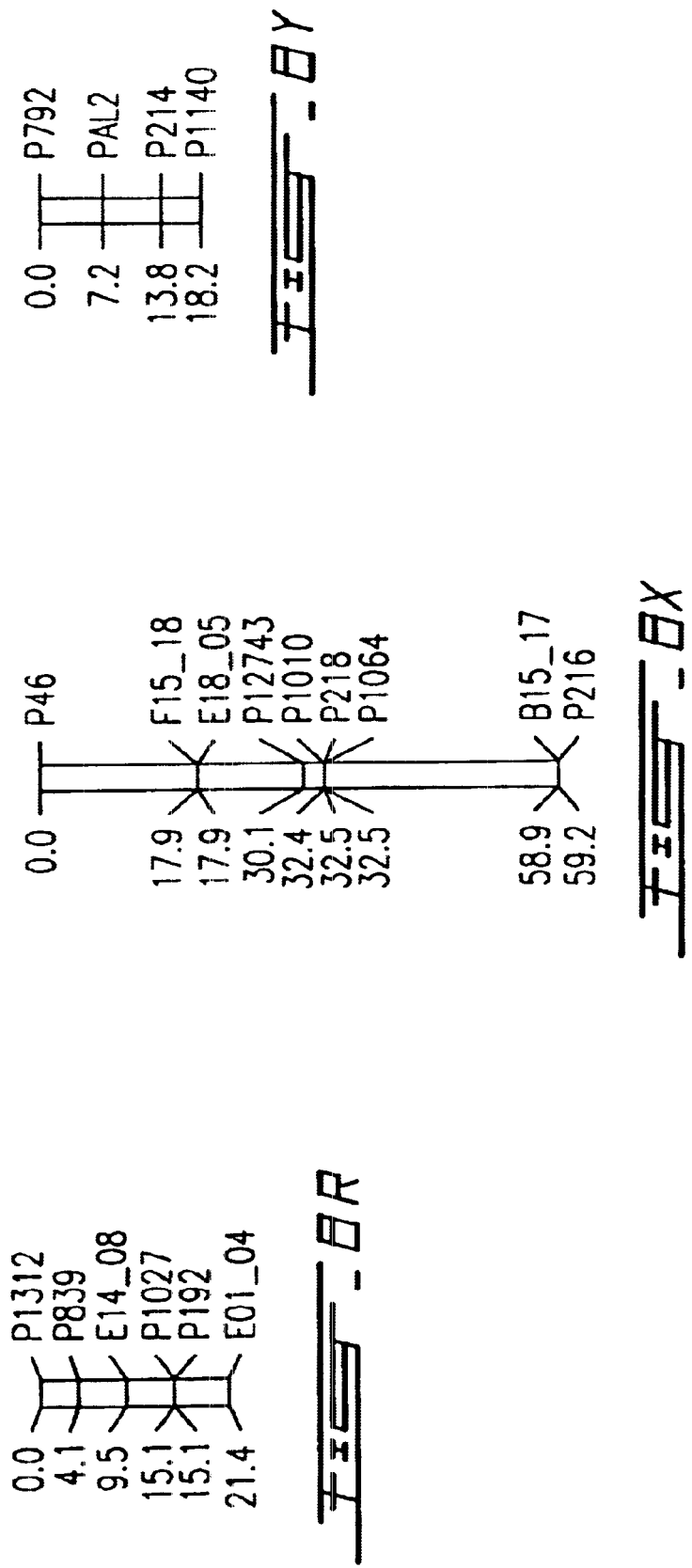

METHOD FOR PREDICTING FIBER LENGTH USING QTL'S AND MOLECULAR MARKERS

This application claims the benefit of provisional application Ser. No. 60/118,103, filed Feb. 1, 1999.

BACKGROUND OF THE INVENTION

1. Field of the Invention

This invention is in the fields of tree breeding and molecular biology, and pulp and paper properties evaluations. This invention allows for an enhanced efficiency of selection for superior trees in both plantation and natural populations, based on fiber length.

2. Description of the Prior Art

Many tree characteristics of commercial importance, such as wood density, volume growth and fiber properties, are known to exhibit continuous levels of variation in both natural and plantation populations [J. E. Eckenwalder. "Systematics and Evolution of Populus" in Biology of Populus (Stettler, R. F., Bradshaw, H. D., Heilman, P. E., & Hinckley, T. M. eds) NRC Research Council Press, Ottawa ON, pp. 7–32 (1996)]. The greatest barrier to progress in selection for quantitative traits is the lack of repeatability of phenotypic traits in different environments. Hence, identifying individuals with the most favorable genotype is one of the most difficult and challenging aspects of tree breeding. The roots of quantitative trait variation lie in the fact that such traits are controlled by not one but several genetic components working together. Despite this complexity, advancing technology in genetic marker development has made it possible to identify the genetic regions which contribute to the control of continuously variable properties. These regions are known as quantitative trait loci or QTL's [E. S. Lander & D. Botstein, *Genetics* 121, 185–199 (1989)]. A genetic marker is any qualitatively inherited phenotype that can be used to monitor the segregation of alleles that are genetically linked to the marker. It is possible to identify and monitor genetic markers that are closely linked to QTLs. In order for a QTL to be identified or mapped to a specific chromosomal location, it must first be demonstrated that the quantitative trait of interest is highly correlated with a genetic marker.

In this fashion, QTLs have been mapped for a number of traits including volume growth, wood density and bud flush date. To this point, however, no properties which directly impinge upon the pulp and paper industry have yet been QTL mapped.

Breeding and selection for enhanced wood and fiber properties in trees has historically been necessarily complex. Traditional approaches to tree improvement suffer from a number of problems. Firstly, the intervals between generations are necessarily long—even fast-growing species (e.g., poplar) must be left for 4–8 years to develop. Secondly, the ability to select trees on the basis of only one or two physical characteristics is limited given the large amount of genetic material involved in crosses and the consequent complexity of the genetic intermixing which occurs.

Similarly, in natural forests, superior trees for industrial use cannot be readily identified without undertaking extensive characterization studies. This invention will help circumvent some of the necessary testing and facilitate the selection of superior tree lines.

SUMMARY OF THE INVENTION

One aim of the present invention is to provide means to circumvent some of the necessary testing and facilitate the selection of superior tree lines.

In accordance with another embodiment of the present invention, there is provided a method of identifying a genetic marker associated with a genetic locus conferring at least one enhanced property selected from the group consisting of fiber length, coarseness, DBH (diameter at breast height), density and yield in a family of trees, which comprises the steps of:

a) obtaining a sexually mature parent tree exhibiting enhanced fiber length properties;

b) obtaining a plurality of progeny trees of the parent tree by performing self or cross-pollination;

c) assessing multiple progeny trees for each of a plurality of genetic markers;

d) identifying genetic markers segregating in an essentially Mendelian ratio and showing linkage with at least some other of the plurality of genetic markers;

e) measuring fiber length in multiple progeny trees; and f) correlating the presence of at least one enhanced property with a least one marker identified in step d) as segregating in an essentially Mendelian ratio and showing linkage with at least some of the other markers, the correlation of the presence of at least one enhanced property with a marker indicating that the marker is associated with a genetic locus conferring an enhanced property; wherein the family of trees comprises a parent tree and its progeny.

In accordance with another embodiment of the present invention there is provided a method of producing a plurality of clonal trees that have at least one enhanced property selected from the group consisting of fiber length, coarseness, DBH, density and yield, which comprises the steps of:

a) obtaining a sexually mature parent tree exhibiting enhanced fiber length properties;

b) obtaining a plurality of progeny trees of the parent tree by performing self or cross-pollination;

c) assessing multiple progeny tress for each of a plurality of genetic markers;

d) identifying genetic markers segregating in an essentially Mendelian ratio and showing linkage with at least some other of the plurality of genetic markers;

e) measuring fiber length in multiple progeny trees;

f) correlating the presence of at least one enhanced property with a least one marker identified in step d) as segregating in an essentially Mendelian ratio and showing linkage with at least some of the other markers;

g) selecting a progeny tree containing a marker identified in step f) as associated with a genetic locus conferring at least one enhanced property; and h) vegetatively propagating the progeny tree selected in step g) to produce a plurality of clonal trees, essentially all of the clonal trees exhibiting at least one enhanced property.

In accordance with another embodiment of the present invention there is provided a method of producing a family of trees wherein at least about half exhibit at least one enhanced property selected from the group consisting of fiber length, coarseness, DBH, density and yield, which comprises the steps of:

a) obtaining a sexually mature parent tree exhibiting enhanced fiber length properties;

b) obtaining a plurality of progeny trees of the parent tree by performing self or cross-pollination;

c) assessing multiple progeny tress for each of a plurality of genetic markers;

d) identifying genetic markers segregating in an essentially Mendelian ratio and showing linkage with at least some other of the plurality of genetic markers;
e) measuring fiber length in multiple progeny trees;
f) correlating the presence of at least one enhanced property with a least one marker identified in step d) as segregating in an essentially Mendelian ratio and showing linkage with at least some of the other markers;
g) selecting a progeny tree containing a marker identified in step f) as associated with a genetic locus conferring at least one enhanced property; and
h) sexually propagating the progeny tree selected in step g) to produce a family of trees, at least about half of the family of trees containing a genetic locus conferring at least one enhanced property and the family of trees exhibiting the at least one enhanced property.

In accordance with one embodiment of the present invention, the method may further comprise constructing a genomic map of the parent tree using the plurality of genetic markers.

The genetic marker loci may be restriction fragment length polymorphism (RFLPs) or random amplified polymorphic DNA (RAPDs) which may in turn be correlated with quantitative traits loci (QTLs).

The parent tree may be the seed parent tree to each of the progeny trees, and leaf or cambium tissue from the progeny trees is assessed for the presence or absence of genetic markers in step c).

The parent tree may be of the genus Populus, more specifically of a species of Populus trichocarpa, Populus deltoides, Populus tremuloides or a hybrid thereof.

In accordance with one embodiment of the present invention, there is provided a genetic map of QTLs of trees of the genus Populus associated with fiber length as set forth in FIG. 8.

In accordance with one embodiment of the present invention, there is provided a genetic marker of fiber length of trees, which comprises a 800 bp amplification product, wherein presence of the product in an amplified DNA sample from the trees is indicative of a short fiber length $\leq 0.92$ mm and absence of the product is indicative of long fiber length $> 0.92$ mm.

For the purpose of the present invention the following terms are defined below.

The term "DBH" is intended to mean diameter (cm) of the tree stem at breast height~1.3 m.

The term "coarseness" is intended to mean a weight to length ratio for fibers (mg/m).

The term "yield" is intended to mean the amount of fiber recovered from a given weight of wood (%).

The term "density" is intended to mean a weight to volume ratio for wood (g/cm$^3$).

The expression "enhanced fiber length properties" is intended to mean a fiber greater than 0.92 mm in length.

The expression "short fiber length" is intended to mean fibers $\leq 0.92$ mm.

The expression "long fiber length" is intended to mean fibers $> 0.92$ mm.

The expression "800 bp amplification product" is intended to mean an amplification product, such as a PCR product, of the RAPD marker G03 of size 800 base pairs.

BRIEF DESCRIPTION OF THE DRAWINGS

FIG. 6 illustrates hierarchical cluster analysis of fiber length data for all 57 clones;

FIG. 7 illustrates ranking of all 57 clones in terms of fiber length;

FIG. 8 illustrates Populus genetic map showing positions of QTLs detected; and

DETAILED DESCRIPTION OF THE INVENTION

Figure 1:
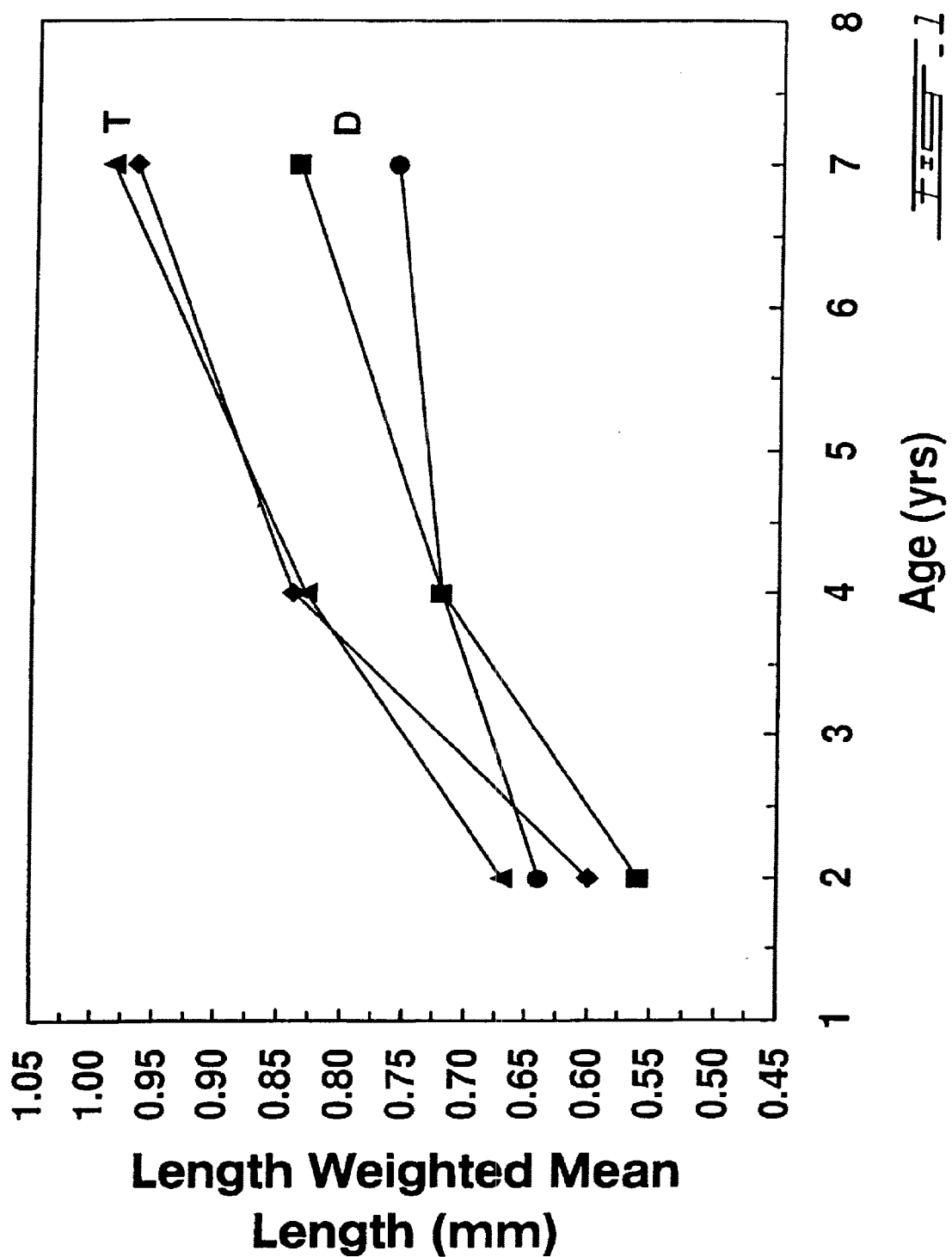
FIG. 1 illustrates fiber length as a function of age for parental clones 14–129 (D) and 93–968 (T)

A number of previous studies [H. D. Bradshaw & R. F. Stettler, *Genetics* 139, 963–973 (1995); R. W. Allard, *Principles of Plant Breeding*. John Wiley & Sons, New York (1960)] have suggested that growth, adaptive and wood quality traits are not controlled by huge numbers of genes with small effects but that they are determined by a few genes with large effects whose influences are tempered by environmental blurring. The method described in this invention demonstrates that this situation holds for fiber property determinants also. Two significant QTLs have been discovered which individually can account for 66.5% and 28.3% of the variance observed in fiber length. Together, therefore, these QTLs explain 94.8% of the variance in fiber length seen at the single sampling site chosen for the experiment.

Potentially, these QTLs can be used for the development of marker-assisted breeding or rapid assessment techniques which could save the pulp and paper industry much time and money in the refinement and development of new and better products based on purpose-grown fiber of known quality. The QTLs can be applied to enhance and direct tree breeding experiments to the improvement of wood quality traits and to the rapid assessment of natural stands on the basis of their fiber properties.

Materials and Methods

Sampling Site

Sampling was conducted at the Washington State University Farm 5 plantation site in Puyallup, Wash. The pedigree sampled was founded in 1981 by interspecific hybridization between *Populus trichocarpa* (clone 93–968) and *P. deltoides* (clone ILL-129). Two siblings from the first hybrid generation (F1 family 53), 53–246 and 53–242, were crossed in 1988 to give rise to a family of second generation hybrids used for genetic mapping studies (F2 family 331). Unrooted cuttings of the P, F1 and 55 F2 clones were planted at Farm 5 in a modified randomized complete block design at a 2×2 m spacing in the spring of 1991.

Tree Sampling

Ten millimeter diameter increment cores were obtained at approximately breast height from each of the 137 surviving trees in the pedigree. All cores were removed through the pith from bark to bark. DNA samples were obtained from live leaf tissue using standard protocols for the Bio101 Fast Prep instrument. PCR reactions were optimized for RAPD analysis according to previously developed methods [H. D. Bradshaw & R. F. Stettler, *Genetics* 139, 963–973 (1995)].

Fiber Properties

The 10 mm increment cores were segregated into two annual growth rings and hand chipped. Fibers for analysis were obtained using an acetic acid/hydrogen peroxide maceration technique [L. F. Burkart, *For. Prod. J.,* 16, 52 (1966)] whereby a known OD weight of chips was first placed in a test tube, saturated with water then covered in maceration solution [1:1 mixture of glacial acetic acid:hydrogen peroxide (30% from stock bottle)]. These samples were then incubated in a dry heating block for 48 hrs. at 60° C. The maceration solution was washed from the chips extensively using distilled water and the pulps disintegrated in a small Hamilton Beech mixer. A dilution series was then used to obtain representative samples of 10–20,000 fibers (corresponding to approximately 5 mg of macerated pulp) which were analyzed for length and coarseness values using a Kajaani FS-200 instrument and/or the Optest Fiber Quality Analyzer.

Genetic Map Construction and QTL Mapping

The Populus genetic map used in this study, previously constructed using the same family 331 pedigree, consists of 342 RFLP, STS and RAPD markers and is previously described [H. D. Bradshaw, M. Villar, B. D. Watson, K. G. Otto & S. Stewart, *Theor. Appl. Genet.* 89, 551–558 (1994)]. The 19 large linkage groups, corresponding closely to the 19 Populus chromosomes, were scanned for the phenotypic data obtained using the program MAPMAKER-QTL 1.1 [A. H. Patterson, S. Damon, J. D. Hewitt, D. Zamir & H. D. Rabinowich, *Nature* 335, 721–726 (1988)]. Based on the scanned genome length and the distance between genetic markers, a logarithmic odds (LOD) significance threshold level of 2.9 was chosen (this ensures that the chance of a false positive QTL being detected is at most 5%). For more details on the QTL mapping procedure employed see [H. D. Bradshaw & R. F. Stettler, *Genetics* 139, 963–973 (1995)].

Results and Discussion

Fiber Properties

Figure 2:
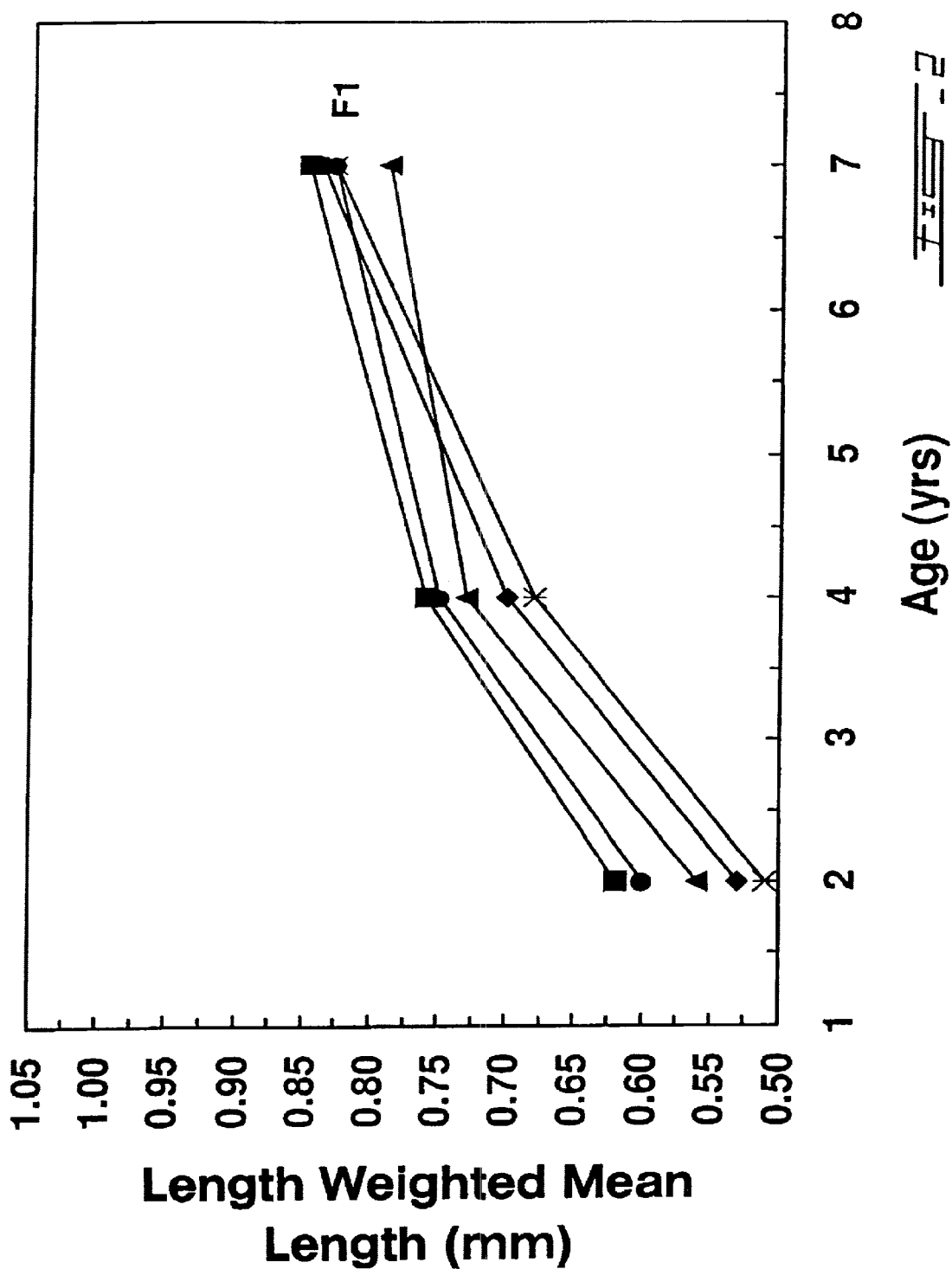
FIG. 2 illustrates fiber length as a function of age for F1 generation clones 53–242 and 53–246.
Figure 3:
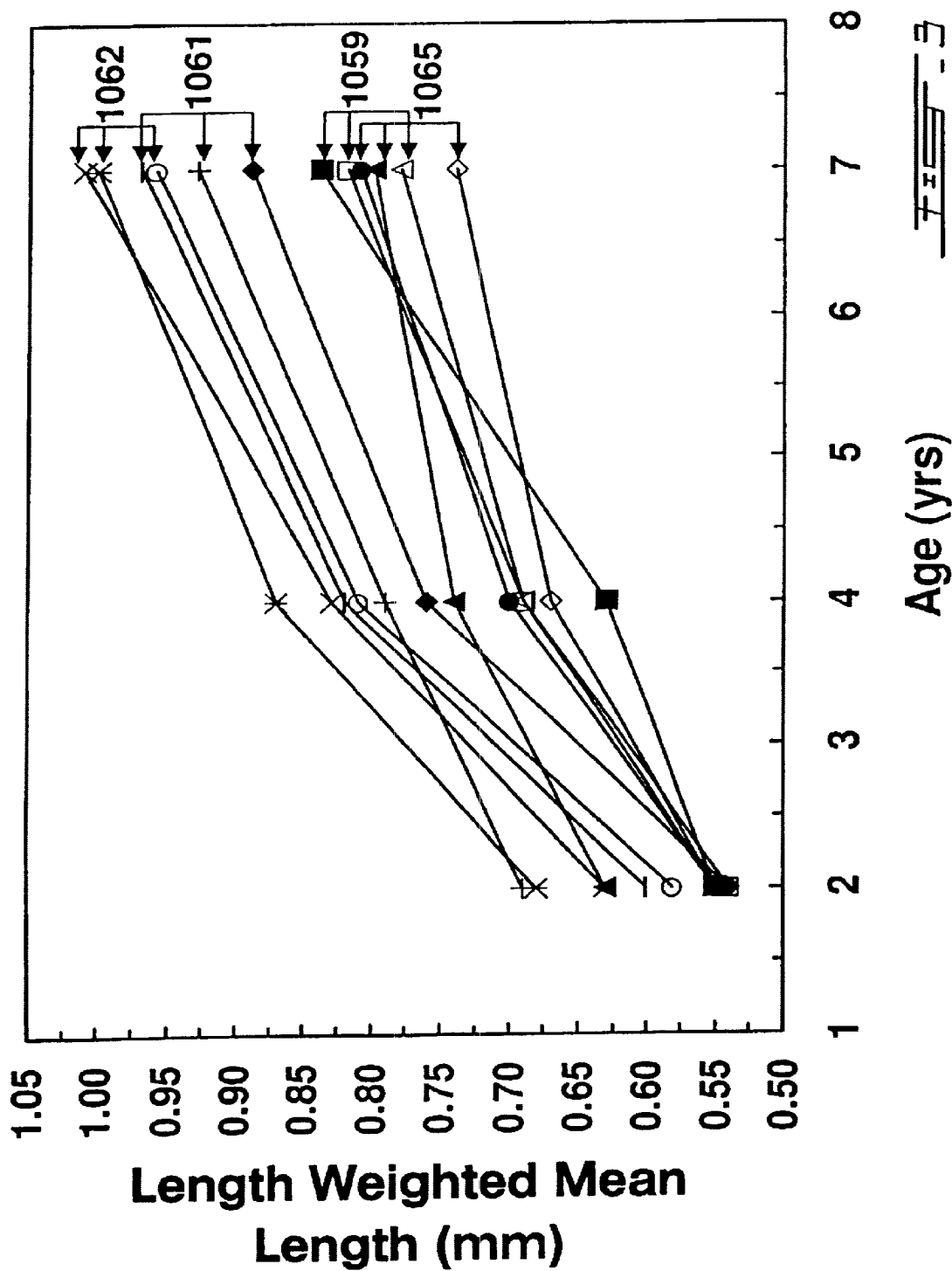
FIG. 3 illustrates fiber length as a function of age for F2 generation clones 331–1059,1061,1062, 1065.

To facilitate the analysis of fiber properties, an initial subsample consisting of the following 8 clones, the parental species (93–968, ILL-129), the F1 hybrids (53–242, 53–246) and four F2 second generation hybrids (331–1059, 1061, 1062, 1065), were fully characterized. Length-weighted fiber length values for each of these clones are summarized in Table I and are plotted against tree age in FIGS. 1, 2, and 3. As a result of these findings, it was decided that for the remaining clones only the 7$^{th}$ growth ring fiber properties would be analyzed.

TABLE I

Length weighted average fiber lengths for annual increments, mm

| Clone ID | Year 0–2 | Year 3–4 | Year 5–7 |
| --- | --- | --- | --- |
| ILL-129 | 0.60 (±0.06) | 0.72 (±0.00) | 0.80 (±0.06) |
| 93-968 | 0.65 (±0.04) | 0.83 (±0.01) | 0.98 (±0.01) |
| 53-242 | 0.59 (±0.03) | 0.75 (±0.02) | 0.82 (±0.03) |
| 53-246 | 0.52 (±0.01) | 0.69 (±0.01) | 0.84 (±0.01) |

TABLE I-continued

Length weighted average fiber lengths for annual increments, mm

| Clone ID | Year 0–2 | Year 3–4 | Year 5–7 |
| --- | --- | --- | --- |
| 331-1059 | 0.58 (±0.05) | 0.68 (±0.06) | 0.79 (±0.05) |
| 331-1061 | 0.60 (±0.08) | 0.79 (±0.03) | 0.93 (±0.04) |
| 331-1062 | 0.64 (±0.04) | 0.84 (±0.03) | 0.99 (±0.02) |
| 331-1065 | 0.55 (±0.01) | 0.69 (±0.01) | 0.80 (±0.02) |

It is clear from these data that fiber length is still increasing with time at age 7 in this family. The data also show that the two parental lines used to generate the family (D parent ILL-129, T parent 93–968) have, at age 7, statistically significantly different fiber lengths. The F1 progeny (53–242 and 53–246) exhibit similar length-weighted fiber lengths to the D parent. These results suggest that this property is segregating amongst the progeny, particularly in the second generation hybrids and, furthermore, that fiber length in this family is, at least partially, under genetic control.

Figure 4:
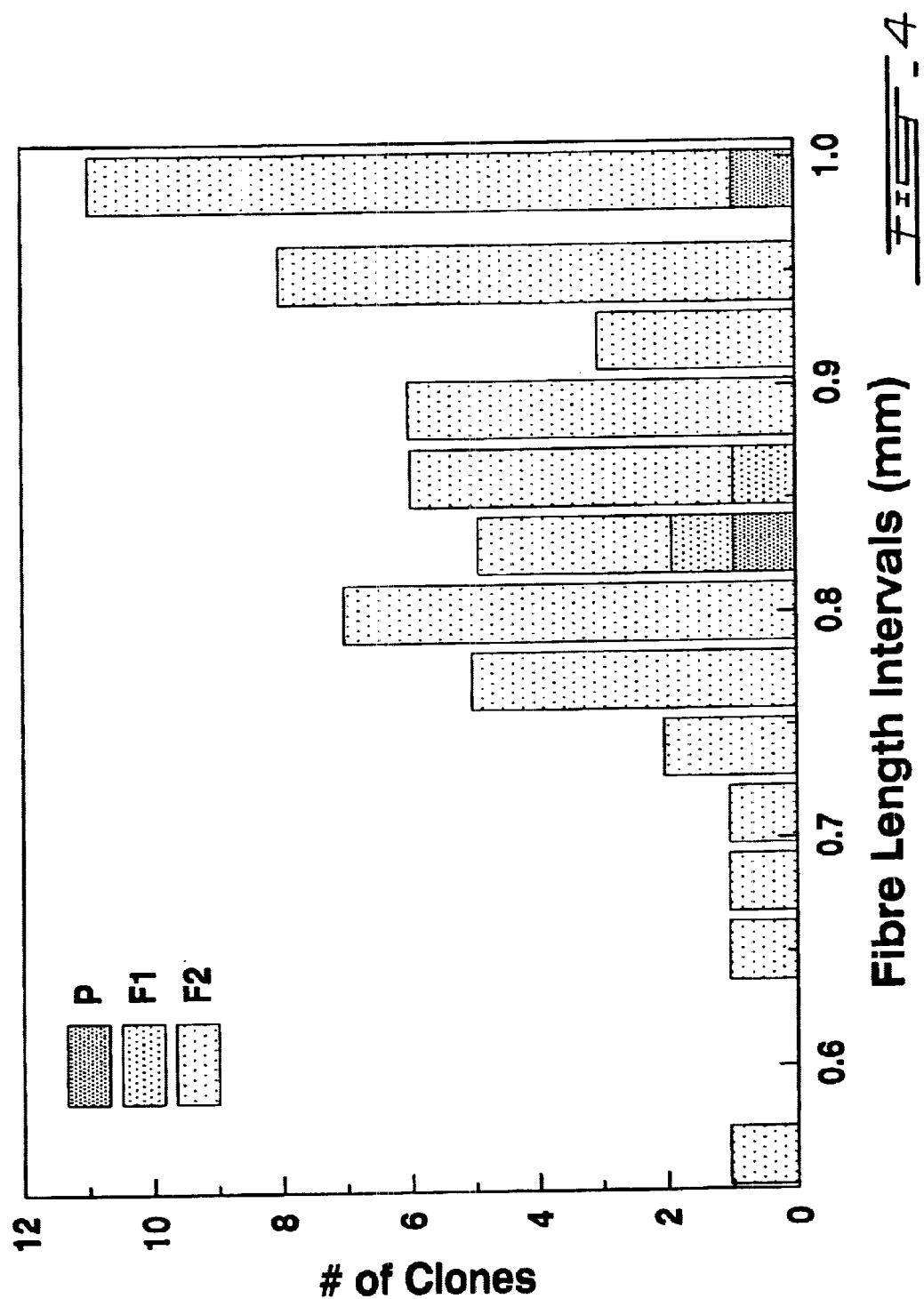
FIG. 4 illustrates fiber length distribution for all 57 clones.

The distribution of the fiber lengths found for each F2 clone is presented in FIG. 4. It can be seen that there is indeed evidence for a bi-modal distribution of fiber lengths amongst these hybrids with fiber length values clustering around the parental types.

Figure 5:
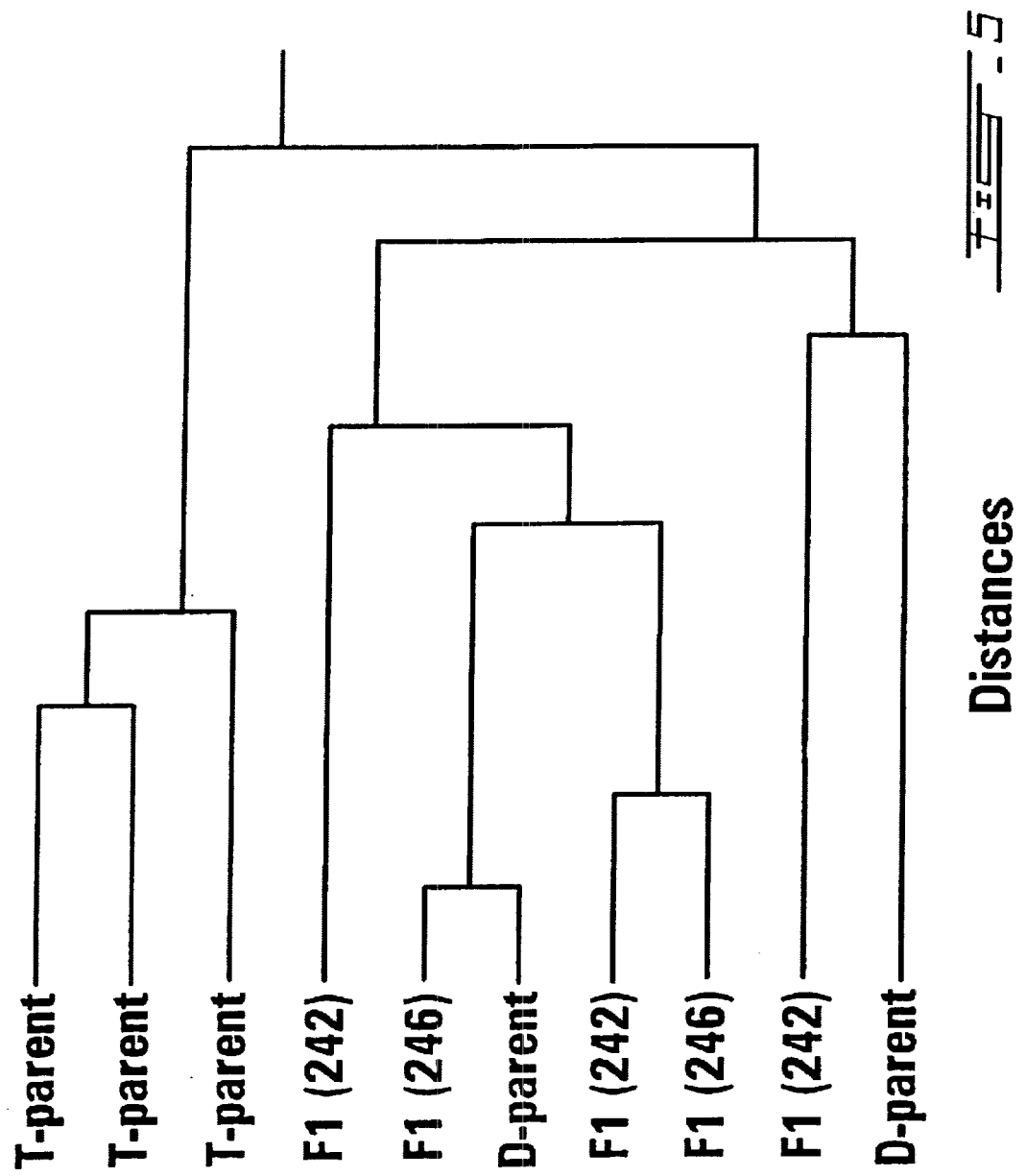
FIG. 5 illustrates hierarchical cluster analysis of fiber length data for parental and F1 generation clones.

The fiber lengths obtained for all clones were then subjected to hierarchical cluster analysis using SYSTAT 7.0. Parental and F1 generation clusters are shown in FIG. 5. The cluster tree for all 57 clones is shown in FIG. 6. FIG. 7 illustrates how the different clusters of clones relate to one another in terms of their fiber lengths. Groups are statistically significantly different from one another as determined by cluster analysis (variation within groups<variation between groups).

QTL Mapping of Fiber Length and Stem Growth Determinants

Regions of DNA which contain multiple genes affecting the same physical trait are known as quantitative trait loci (QTLs). These regions are detected using genetic marker technology and their presence or absence can be statistically correlated in tree populations with the magnitude of a particular physiological trait, such as fiber length. This statistical association is based on the technique of multiple simultaneous linear regressions of trait data with genetic marker presence/absence data using computer software. In this way, genetic maps can be "scanned" for groups of markers which seem to correlate with the trait of interest—this group of markers is then classified as bounding a QTL partially controlling that trait (in other words, the markers are not the genes involved in the control of the trait, but those genes exist within the region of DNA bounded by the markers—this method is known as interval mapping). The degree of association between the markers and the trait can be used to estimate the "strength" of the QTL, i.e., the percentage of the trait variance which that particular QTL can account for.

Using fiber length data obtained from the family 331 pedigree, the hybrid poplar genetic map [H. D. Bradshaw & R. F. Stettler, *Genetics* 139, 963–973 (1995)] was scanned with MAPMAKER-QTL 1.1 [H. D. Bradshaw & R. F. Stettler, *Genetics* 139, 963–973 (1995)]. Details on each of the QTLs detected are summarized in Table II and their positions on the Populus genetic map are indicated in FIG. 8. Boxes A–Y represent linkage groups functionally equivalent to the 19 populus chromosomes. The identities (e.g. P1277) and positions of each genetic marker assigned to the map are indicated on the boxes.

TABLE II

Fiber length QTLs
Fiber Length for 6-year old hybrids

| Trait | Marker/Linkage Group | LOD | Phen % | Mean TT | TD | DD | Dom. |
|---|---|---|---|---|---|---|---|
| Fiber length | | | | | | | |
| FL-2 | E18_15-CO1_16/M | 3.09 | 66.5 | 0.828 | 0.925 | 0.759 | 0.1313 |
| FL-3 | G12_09-G03_14/O | 3.22* | 28.3 | 0.935 | 0.849 | 0.795 | −0.0160 |

*Maps to similar location as other growth and form QTLs previously determined [R. W. Allard, Principles of Plant Breeding. John Wiley & Sons, New York (1960)].
LOD = Logarithmic odds score (reflects probability of QTL).
Phen. = % phenotypic variance explained by QTL.
Dom. = The dominance effect of the D allele.

The two fiber length QTLs exceeded the threshold LOD score of 2.9 which implies that these QTLs are above the 95% probability threshold. Hence the associated genetic markers may now be selected for further study as possible indicators for rapid assessment and molecular breeding experiments. There is a close relationship between this family and other members of Populus genus and it is likely that these markers and associated QTLs will also be applicable to species such as aspen.

Genetic Control of Fiber Properties

The two parental species used to generate the hybrid family used in this study have statistically significantly different fiber lengths. These parental fiber types are seen to segregate amongst their progeny giving rise to a bimodal distribution of fiber length throughout the F2 generation. The F1 generation all exhibit D-parent fiber lengths. Given that all of the trees in the pedigree have been grown under the same environmental conditions, these observations strongly suggest that fiber properties are under at least moderate genetic control. Heritability ($H^2$) is a measure of the degree of genetic control of a trait. A $H^2$ value of 0.50, for example, implies that the trait of interest is 50% under genetic control. The other half of the trait variability is controlled by environmental factors. A heritability ($H^2$) estimate for fiber length was obtained using a general linear model method within SYSTAT 7.0. Calculated according to the relationship ($H^2$) ($MS_{clone} - MS_{rep.\ clone}$)/MS clone, (where MS=Type III mean squares), the broad sense heritability of fiber length in this family was estimated to be 0.47. In eucalyptus $H^2$ estimates for fiber length have ranged from 0.12 [G. O. Otegbeye and R. C. Kellison, Sylvae Genetica 29, 27 (1980)] to 0.59 [C. R. E. Clarke, Msc. Thesis, University of Natal, Pietermaritzburg, South Africa (1990)].

The present invention will be more readily understood by referring to the following examples which are given to illustrate the invention rather than to limit its scope.

EXAMPLE I

Determination of Fiber Length of Trees

Figure 9:
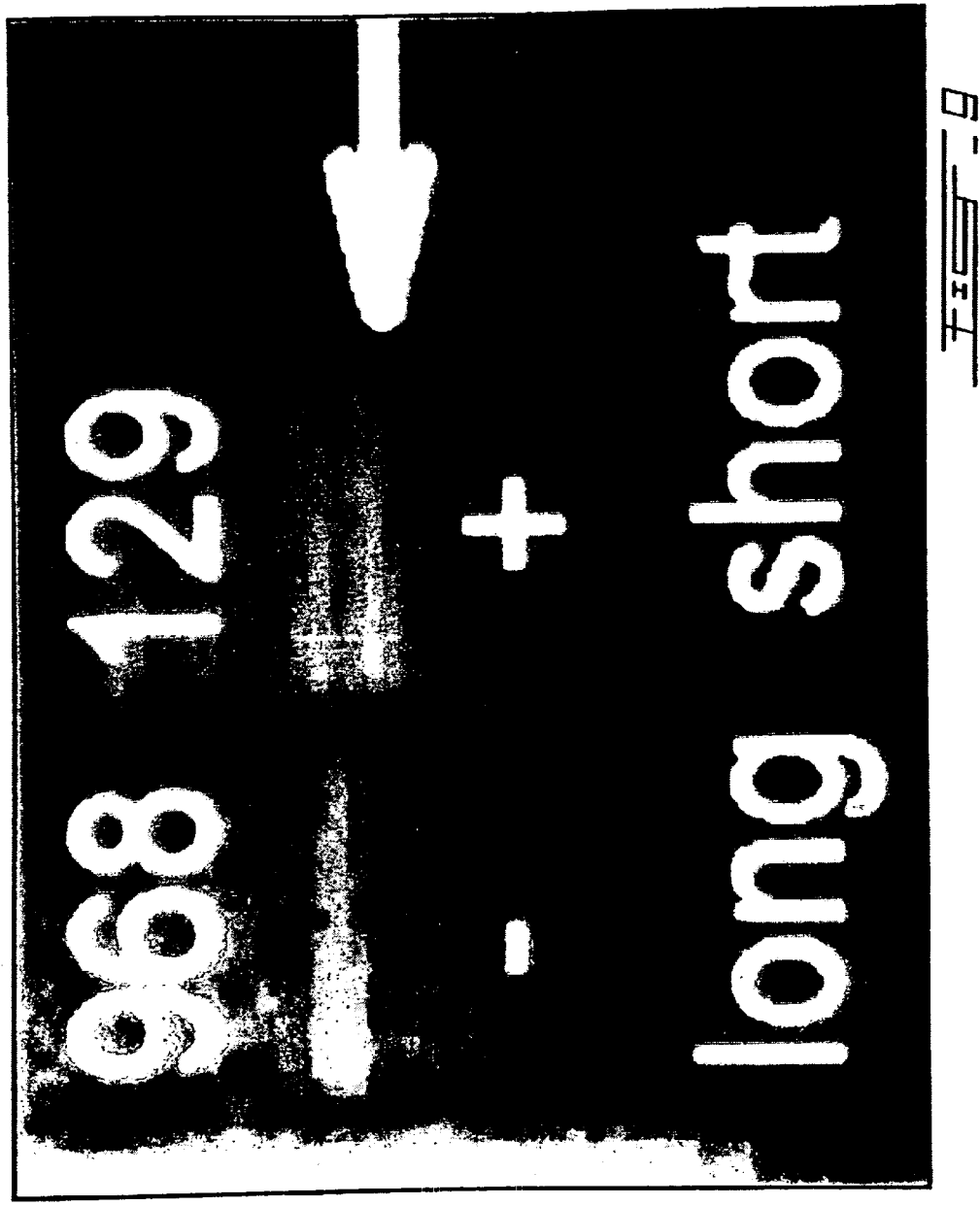
FIG. 9 illustrates the 800 bp G03 RAPD product predictive of fiber length in Family 331.

A preliminary experiment to demonstrate the potential of this technology in the development of rapid assessment techniques has been undertaken using a QTL-associated genetic marker in a predictive capacity to screen a series of unknown samples for fiber length properties. Genomic DNA was isolated from a series of aspen samples taken from three different sites in central British Columbia, D, F and K. These DNA templates were then selectively amplified by polymerase chain reaction (PCR) using the QTL-associated genetic marker G03 and the patterns were assessed for the presence or absence of a~800 bp PCR product. This product, based on previous studies on the family 331 hybrid poplar clones, is thought to qualitatively co-vary with fiber length. The presence of the product in the amplified DNA of a clone in family 331 coincides with shorter fibers; the absence with longer fibered clones. Fiber length predictions (long or short) for each aspen clone were then made based on these assessments. The actual fiber length properties of the test aspen clones were subsequently determined by conventional means and compared to the DNA-based method predictions. FIG. 9 shows the 800 bp product indicative of relative fiber length in family 331 clones. Clone 968 (trichocarpa) has longer fibers (0.99 mm); clone 129 (deltoides) has shorter fibers (0.85 mm).

Table III shows the results of the predictive DNA tests for the unknown aspen series and the actual fiber properties for those trees as determined by conventional pulping means. In each case, it can be seen that the predictions based on the 800 bp PCR product are accurate.

TABLE III

PCR-based predictive fiber length analysis for unknown aspen clones

| Clone ID | 800 bp G03 fragment | Predicted long/short* | FS-200 Fiber Length (mm) |
|---|---|---|---|
| K3-3 | − | Long | 1.06 |
| K3-4 | − | Long | 1.10 |
| K6-1 | + | Short | 0.82 |
| K6-2 | + | Short | 0.83 |
| K7-2 | − | Long | 1.06 |
| K7-3 | − | Long | 1.02 |
| F2-1 | − | Long | 1.04 |
| F2-2 | − | Long | 1.08 |
| F4-1 | + | Short | 0.84 |
| F4-2 | + | Short | 0.86 |
| F5-1 | + | Short | 0.82 |
| F5-4 | + | Short | 0.80 |
| F7-1 | − | Long | 0.99 |
| F7-3 | + | Short | 0.81 |
| F7-4 | + | Short | 0.88 |
| F8 | + | Short | 0.73 |
| D1-14 | − | Long | 1.01 |
| D1-19 | − | Long | 1.00 |
| D3-5 | + | Short | 0.85 |

*Predictions of long or short fibers in the aspen clones tested are relative and are based on two statistically significantly different fiber length groups found amongst natural aspen populations (1.05 mm and 0.85 mm).

Table IV presents complete data sets for fiber length at age 7 valves for each clone in the study. Clones are identified according to family and individual gerotype numbers (specific replicates are also indicated).

TABLE IV

Complete data for individual clones of mapping population

| Clone ID | Rep | FL (mm) | DBH (cm) | Density (g/cm³) | Yield % | Coarseness (mg/m) |
|---|---|---|---|---|---|---|
| 14-129 | A | 0.84 | 8.9 | 0.28 | 46.2 | 0.065 |
| 14-129 | C | 0.76 | 11.5 | | 44.1 | 0.085 |
| 93-968 | A | 0.99 | 26.9 | | 50.8 | 0.095 |
| 93-968 | B | 0.97 | 28.5 | 0.3 | 49.9 | 0.112 |
| 93-968 | C | 0.98 | 25.8 | 0.29 | 50.5 | 0.102 |
| 53-242 | A | 0.85 | 34.7 | | 50.9 | 0.082 |
| 53-242 | B | 0.83 | 35.1 | 0.33 | 47 | 0.069 |
| 53-242 | C | 0.79 | 34.2 | 0.34 | 52.4 | 0.076 |
| 53-246 | C | 0.83 | 30.7 | 0.31 | 50.9 | 0.065 |
| 53-246 | D | 0.84 | 26.6 | | 46.8 | 0.082 |
| 331-1059 | A | 0.83 | 19.2 | | 55.9 | 0.083 |
| 331-1059 | B | 0.74 | 22.2 | 0.33 | 47.6 | 0.075 |
| 331-1059 | C | 0.8 | 22 | 0.37 | 56.1 | 0.079 |
| 331-1061 | A | 0.96 | 13 | | 51.8 | 0.095 |
| 331-1061 | B | 0.89 | 8.1 | 0.32 | 43.4 | 0.086 |
| 331-1061 | C | 0.93 | 13.9 | 0.37 | 50.7 | 0.098 |
| 331-1062 | A | 1.01 | 24.2 | | 49.3 | 0.102 |
| 331-1062 | B | 1 | 19 | 0.28 | 45.5 | 0.118 |
| 331-1062 | C | 0.97 | 16.1 | 0.3 | 39.7 | 0.095 |
| 331-1065 | A | 0.78 | 13.2 | | 45.8 | 0.088 |
| 331-1065 | B | 0.82 | 17.7 | 0.29 | 50.8 | 0.076 |
| 331-1065 | C | 0.81 | 13 | 0.3 | 55.8 | 0.055 |
| 331-1060 | A | 0.85 | 15 | 0.28 | 47.8 | 0.1037 |
| 331-1060 | C | 0.81 | 14.2 | 0.32 | 51.8 | 0.089 |
| 331-1064 | A | 0.98 | 10.8 | 0.35 | 55.9 | 0.064 |
| 331-1064 | C | 0.96 | 10.9 | 0.36 | 48.9 | 0.083 |
| 331-1067 | A | 0.82 | 12.4 | 0.31 | 52.3 | 0.064 |
| 331-1067 | B | 0.87 | 15 | 0.29 | 47.6 | 0.063 |
| 331-1067 | C | 0.87 | 9.5 | 0.31 | 53.2 | 0.066 |
| 331-1069 | A | 0.89 | 16.1 | 0.38 | 49.6 | 0.095 |
| 331-1069 | B | 0.99 | 17.4 | 0.38 | 56.1 | 0.1131 |
| 331-1072 | C | 0.84 | 13.2 | 0.3 | 49.6 | 0.054 |
| 331-1073 | B | 0.69 | 12.7 | 0.41 | 54.4 | 0.061 |
| 331-1075 | A | 0.91 | 18.3 | 0.34 | 51.8 | 0.092 |
| 331-1075 | B | 0.88 | 20.5 | 0.34 | 51 | 0.097 |
| 331-1075 | C | 0.91 | 17.7 | 0.32 | 54.7 | 0.085 |
| 331-1076 | A | 0.74 | 10.8 | 0.34 | 43.4 | 0.068 |
| 331-1076 | C | 0.76 | 11.3 | 0.32 | 53.6 | 0.085 |
| 331-1077 | C | 0.77 | 6.4 | 0.34 | 54.2 | 0.038 |
| 331-1078 | A | 0.87 | 17.9 | 0.35 | 50.7 | 0.085 |
| 331-1078 | B | 0.85 | 16.5 | 0.38 | 51 | 0.08 |
| 331-1079 | A | 0.98 | 10.9 | 0.34 | 55.6 | 0.085 |
| 331-1079 | B | 0.89 | 14.1 | 0.34 | 49.3 | 0.1 |
| 331-1079 | C | 0.95 | 17.9 | 0.34 | 47.6 | 0.092 |
| 331-1084 | A | 0.91 | 14.2 | 0.38 | 51.3 | 0.085 |
| 331-1084 | C | 0.85 | 16.3 | 0.38 | 45.5 | 0.074 |
| 331-1086 | A | 0.82 | 15.2 | 0.32 | 44.1 | 0.083 |
| 331-1086 | B | 0.87 | 14.9 | 0.32 | 48.9 | 0.079 |
| 331-1087 | A | 0.86 | 15.6 | 0.35 | 39.7 | 0.079 |
| 331-1087 | B | 0.85 | 16.2 | 0.36 | 39.3 | 0.066 |
| 331-1087 | C | 0.84 | 16.3 | 0.42 | 54.6 | 0.085 |
| 331-1090 | A | 0.95 | 10.8 | 0.33 | 45 | 0.076 |
| 331-1093 | A | 0.91 | 11.6 | 0.32 | 44.5 | 0.085 |
| 331-1093 | B | 0.75 | 9.1 | 0.31 | 48.5 | 0.085 |
| 331-1093 | C | 0.81 | 10.6 | 0.3 | 45.8 | 0.065 |
| 331-1095 | B | 0.91 | 14 | 0.39 | 49.1 | 0.068 |
| 331-1095 | C | 0.77 | 6.6 | 0.39 | 50.8 | 0.091 |
| 331-1101 | A | 0.93 | 17 | 0.36 | 47.2 | 0.095 |
| 331-1101 | B | 0.96 | 16.2 | 0.36 | 55.2 | 0.082 |
| 331-1101 | C | 0.92 | 15 | 0.33 | 55.8 | 0.076 |
| 331-1102 | A | 0.73 | 5 | 0.34 | 43.5 | 0.073 |
| 331-1102 | B | 0.82 | 9.4 | 0.35 | 47.7 | 0.083 |
| 331-1103 | A | 0.81 | 6.2 | 0.32 | 46.2 | 0.085 |
| 331-1103 | B | 0.92 | 15.6 | 0.32 | 49.6 | 0.09 |
| 331-1103 | C | 0.95 | 12 | 0.33 | 50.7 | 0.081 |
| 331-1104 | A | 0.81 | 6.4 | 0.31 | 44.1 | 0.066 |
| 331-1104 | B | 0.82 | 6.8 | 0.31 | 51.5 | 0.054 |
| 331-1106 | A | 0.68 | 7 | 0.31 | 52 | 0.075 |
| 331-1106 | B | 0.79 | 11.5 | 0.33 | 50.8 | 0.068 |
| 331-1112 | A | 0.6 | 9.2 | 0.33 | 48.2 | 0.077 |
| 331-1112 | B | 0.75 | 12.2 | 0.31 | 50.8 | 0.078 |
| 331-1112 | C | 0.76 | 11.5 | 0.35 | 49.9 | 0.065 |
| 331-1114 | A | 0.87 | 9.9 | 0.26 | 51.3 | 0.102 |
| 331-1114 | B | 0.98 | 15.1 | 0.32 | 48.1 | 0.099 |
| 331-1114 | C | 0.99 | 17.4 | 0.32 | 50.5 | 0.118 |
| 331-1118 | A | 0.81 | 13.8 | 0.37 | 46.9 | 0.098 |
| 331-1118 | B | 0.99 | 13.4 | 0.41 | 51 | 0.078 |
| 331-1120 | C | 0.83 | 3.1 | 0.31 | 50.9 | 0.065 |
| 331-1121 | B | 0.54 | 6.8 | 0.35 | 48.2 | 0.055 |
| 331-1122 | A | 0.84 | 20.4 | 0.31 | 51.9 | 0.062 |
| 331-1122 | B | 0.78 | 13.3 | 0.36 | 47 | 0.077 |
| 331-1122 | C | 0.77 | 16.8 | 0.38 | 45.9 | 0.064 |
| 331-1126 | A | 1.03 | 11.6 | 0.41 | 52.7 | 0.113 |
| 331-1126 | B | 0.98 | 7.3 | 0.43 | 52.4 | 0.099 |
| 331-1126 | C | 0.93 | 15.8 | 0.41 | 44 | 0.098 |
| 331-1127 | A | 0.87 | 10.5 | 0.35 | 47.2 | 0.102 |
| 331-1127 | B | 1.01 | 12.8 | 0.34 | 50.9 | 0.124 |
| 331-1127 | C | 1.02 | 12.3 | 0.35 | 48.4 | 0.075 |
| 331-1128 | A | 0.9 | 17.6 | 0.32 | 53.2 | 0.085 |
| 331-1128 | B | 0.85 | 15.3 | 0.33 | 46.8 | 0.085 |
| 331-1128 | C | 0.85 | 16.5 | 0.36 | 39.7 | 0.082 |
| 331-1130 | A | 0.85 | 18.7 | 0.37 | 47.8 | 0.083 |
| 331-1130 | B | 0.92 | 18.2 | 0.35 | 48.9 | 0.079 |
| 331-1130 | C | 0.93 | 16.5 | 0.35 | 51.8 | 0.103 |
| 331-1131 | A | 0.99 | 17.5 | 0.31 | 44.1 | 0.098 |
| 331-1131 | C | 0.96 | 13.8 | 0.31 | 55.9 | 0.085 |
| 331-1133 | A | 0.76 | 7.7 | 0.39 | 45.5 | 0.078 |
| 331-1133 | B | 0.69 | 5 | 0.36 | 48.9 | 0.069 |
| 331-1136 | A | 0.64 | 11.3 | 0.32 | 51.3 | 0.077 |
| 331-1136 | B | 0.69 | 15.5 | 0.36 | 52.3 | 0.082 |
| 331-1140 | A | 0.8 | 13.3 | 0.32 | 56.1 | 0.081 |
| 331-1140 | B | 0.78 | 15.2 | 0.34 | 54.2 | 0.086 |
| 331-1149 | A | 0.91 | 16.2 | 0.34 | 51 | 0.123 |
| 331-1149 | B | 0.94 | 16.1 | 0.33 | 46.9 | 0.122 |
| 331-1149 | C | 0.94 | 14.4 | 0.35 | 55.2 | 0.118 |
| 331-1151 | A | 0.77 | 6.8 | 0.35 | 45.8 | 0.042 |
| 331-1151 | B | 0.94 | 15 | 0.35 | 47.6 | 0.106 |
| 331-1151 | C | 0.91 | 13.6 | 0.35 | 54.4 | 0.117 |
| 331-1158 | A | 0.75 | 7.5 | 0.33 | 48.1 | 0.064 |
| 331-1158 | B | 0.7 | 5.2 | 0.36 | 51 | 0.083 |
| 331-1158 | C | 0.77 | 9.8 | 0.34 | 52 | 0.075 |
| 331-1162 | A | 0.81 | 10.1 | 0.35 | 50.7 | 0.078 |
| 331-1162 | B | 0.89 | 13.5 | 0.34 | 47.2 | 0.087 |
| 331-1162 | C | 0.94 | 11.6 | 0.36 | 52.4 | 0.085 |
| 331-1163 | B | 0.62 | 10.7 | 0.37 | 50.5 | 0.05 |
| 331-1163 | C | 0.65 | 10.5 | 0.4 | 48.3 | 0.054 |
| 331-1169 | A | 0.71 | 12.6 | 0.33 | 44.8 | 0.085 |
| 331-1169 | B | 0.78 | 16.8 | 0.32 | 47.9 | 0.091 |
| 331-1169 | C | 0.8 | 13.5 | 0.32 | 45.9 | 0.121 |
| 331-1173 | A | 0.96 | 14.5 | 0.3 | 49.9 | 0.092 |
| 331-1173 | B | 0.81 | 12.6 | 0.31 | 49.1 | 0.075 |
| 331-1173 | C | 0.91 | 14.5 | 0.29 | 50.8 | 0.092 |
| 331-1174 | B | 0.85 | 17.5 | 0.3 | 46.2 | 0.093 |
| 331-1174 | C | 0.88 | 18.6 | 0.34 | 51.2 | 0.124 |
| 331-1182 | B | 0.88 | 7 | 0.3 | 47.6 | 0.091 |
| 331-1186 | A | 0.91 | 14.5 | 0.33 | 45.8 | 0.089 |
| 331-1186 | B | 0.95 | 15.8 | 0.32 | 52.6 | 0.084 |
| 331-1186 | C | 0.99 | 11.8 | 0.31 | 44.9 | 0.077 |
| 331-1580 | A | 0.67 | 9.8 | 0.32 | 53.2 | 0.075 |
| 331-1580 | B | 0.72 | 13.4 | 0.32 | 51.7 | 0.081 |
| 331-1580 | C | 0.79 | 17.7 | 0.32 | 48.1 | 0.066 |
| 331-1582 | A | 0.86 | 12.4 | 0.37 | 46.8 | 0.075 |
| 331-1582 | B | 1.01 | 6.8 | 0.35 | 51.6 | 0.068 |
| 331-1582 | C | 0.94 | 7.8 | 0.38 | 47.3 | 0.075 |
| 331-1587 | B | 0.85 | 12 | 0.38 | 52.8 | 0.076 |
| 331-1587 | C | 0.91 | 12.5 | 0.38 | 50.5 | 0.075 |

Clone ID = family #-gerotype #
Rep = location at the Puyallop, WA site;
FL = length weighted fiber length (average of triplicate FQA determinations;
DBM = diameter at breast height.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method of producing a plurality of clonal Populus trees that have at least one enhanced property selected from the group consisting of fiber length, coarseness, diameter at breast height (DBH), density and yield, which comprises the steps of:
   a) obtaining a sexually mature parent Populus tree exhibiting fiber length greater than 0.92 mm;
   b) obtaining a plurality of progeny Populus trees of said parent tree by performing self or cross-pollination;
   c) assessing multiple progeny Populus trees for each of a plurality of genetic markers;
   d) identifying genetic markers segregating in an essentially Mendelian ratio and showing linkage with at least some other of said plurality of genetic markers;
   e) measuring fiber length in multiple progeny Populus trees;
   f) correlating the presence of at least one enhanced property with at least one marker identified in step d) as segregating in an essentially Mendelian ratio and showing linkage with at least some of said other markers;
   g) selecting a progeny Populus tree containing a marker identified in step f) as associated with a genetic locus conferring at least one enhanced property; and
   vegetatively propagating said progeny Populus tree selected in step g) to produce a plurality of clonal Populus trees, essentially all of said clonal Populus trees exhibiting at least one enhanced property.

2. The method of claim 1, further comprising constructing a QTL map of said parent tree using said plurality of genetic markers.

3. The method of claim 1, wherein said genetic marker loci are restriction fragment length polymorphism (RFLPs) and or random amplified polymorphic DNA (RAPDs).

4. The method of claim 3, wherein said restriction fragment length polymorphism (RFLPs) or random amplified polymorphic DNA (RAPDs) are correlated with quantitative trait loci (QTLs), and presence of an 800 bp PCR amplification product of RAPD marker G03 is indicative of a short fiber length.

5. The method of claim 1, wherein said parent tree is the seed parent tree to each of said progeny trees, and leaf or cambium tissue from said progeny trees is assessed for the presence or absence of genetic markers in step c).

6. The method of claim 1, wherein said parent tree is a species selected from the group consisting of *Populus trichocarpa, Populus deltoides, Populus tremuloides* and a hybrid thereof.

* * * * *